(12) United States Patent
Williams et al.

(10) Patent No.: US 7,306,459 B1
(45) Date of Patent: Dec. 11, 2007

(54) METHOD AND APPARATUS FOR FILLING A DENTAL ROOT CANAL

(75) Inventors: Jill Ann Williams, Thorpe (GB); David John Clements, Crawley Down (GB); Gavin John Pearson, Reading (GB); Michael Wilson, London (GB)

(73) Assignee: Denfotex Ltd., London (GB)

( * ) Notice: Subject to any disclaimer, the term of this patent is extended or adjusted under 35 U.S.C. 154(b) by 0 days.

(21) Appl. No.: 11/085,785

(22) Filed: Mar. 21, 2005

Related U.S. Application Data (63) Continuation of application No. 09/980,895, filed on Dec. 3, 2001.

(30) Foreign Application Priority Data

| | | | |
|---|---|---|---|
| Jun. 4, 1999 | (GB) | ................... | 9913100.5 |
| Jan. 14, 2000 | (GB) | ................... | 0000882.1 |
| Jan. 14, 2000 | (GB) | ................... | 0000887.2 |

(51) Int. Cl.
*A61C 1/00* (2006.01)
*A61C 5/02* (2006.01)

(52) U.S. Cl. ................. 433/29; 433/217.1; 433/224

(58) Field of Classification Search ............. 433/224, 433/29, 81, 102
See application file for complete search history.

(56) References Cited

U.S. PATENT DOCUMENTS

| | | | | |
|---|---|---|---|---|
| 4,813,876 A | * | 3/1989 | Wang | .......................... 433/224 |
| 4,979,900 A | * | 12/1990 | Okamoto et al. | ............ 433/224 |
| 5,116,227 A | * | 5/1992 | Levy | ............................ 433/216 |
| 5,149,268 A | * | 9/1992 | Johnson | ....................... 433/224 |
| 5,611,793 A | * | 3/1997 | Wilson et al. | .................. 606/2 |
| 5,941,701 A | * | 8/1999 | Moran et al. | ................... 433/1 |

FOREIGN PATENT DOCUMENTS

| | | | |
|---|---|---|---|
| DE | 8517634.6 | * | 6/1985 |
| EP | 0830850 | | 3/1998 |
| EP | 0830851 A1 | * | 3/1998 |
| WO | WO93/21992 | * | 11/1993 |

* cited by examiner

*Primary Examiner*—Todd E. Manahan
(74) *Attorney, Agent, or Firm*—Connolly Bove Lodge and Hutz (57) ABSTRACT

A method of filling a dental root canal is disclosed herein. The method includes gaining access to the dental root canal and introducing a flowable photosensitizer into the dental root canal. After introducing the flowable photosensitizer into the dental root operation is performed for activating the flowable photosensitizer by exposing the walls of the dental root canal to light via an optical fiber within the dental root canal. Activating the flowable photosensitizer at least partially kills bacteria within the dental root canal and pulp chamber. After activating the flowable photosensitizer, the dental root canal is obturated.

35 Claims, 5 Drawing Sheets

LIGHT DETECTED VS. THICKNESS FOR HORIZONTAL DISCS OF DENTINE FOR VARIOUS PROCESSING TIMES

METHOD AND APPARATUS FOR FILLING A DENTAL ROOT CANAL

CROSS REFERENCE TO RELATED APPLICATIONS

This is a Continuation of U.S. patent application Ser. No. 09/980,895, entitled "Method And Apparatus For Filling a Dental Root Canal" that was filed on Dec. 3, 2001 now abandoned. This application claims the benefit of International Application Published under the Patent Cooperation Treaty (PCT) having International Publication Number WO00/74587 filed Jun. 2, 2000 entitled "Method And Apparatus For Filling a Dental Root Canal," of common assignee herewith.

FIELD OF THE INVENTION

This invention relates to the treatment of a dental root canal including the obturation of the canal.

BACKGROUND OF THE INVENTION

There are a number of situations in which treatment of root canals in teeth is indicated. The tissue lying within the tooth structure, the dental pulp, may become diseased as a result of dental caries or the cells and tissue may be traumatised or atrophy. As a result of this, the pulp tissue may die and/or become infected. This leads to death of the pulp. While it has been common practice to extract the tooth, use of the tooth can be preserved by the removal of the diseased tissue and sealing the cleaned and sterilised canal. The operation of mechanically removing the diseased pulp is technically difficult and require the accessing of the canal and removing infected tissue, which may be at or near the apex of the root of the tooth. The treatment becomes more complex as the anatomy of the root canal becomes more complex and the canals themselves become narrower.

Conventional endodontic treatment involves first gaining access to the pulp chamber by removing the overlying enamel and dentine. Once the pulp chamber is exposed, the entrances to the root canals are then located and enlarged. The length of the root canal is calculated from a diagnostic radiograph or by means of an apex locator and the canal is instrumented using files and/or reamers of increasing size. These instruments are designed to remove the internal surface of the root canal by rasping and cutting the dentine walls. The dentine walls have small holes where the dentine forming cell processes track into the dentine. These holes are sites where bacteria can settle and proliferate. It is these areas which are reduced by mechanical debriding of the internal surface of the root canal. To achieve this, the reamers and files are used to produce a root canal that, near the apex, is matched in size to the obturating device. The internal diameter of the canal is enlarged so that the cavities in the root wall are reduced in size and the canal is mechanically cleaned.

Medicaments may be used to chemically kill the bacteria; these are usually disinfectants and anti-bacterials such as hypochlorite solution or antibiotic pastes. These may be introduced into the root canal after initial mechanical debridement. These medicaments and mechanical methods of removal of tissue are designed to produce a root canal which is free of bacteria and other contaminants. Conventional procedures are time consuming and difficult to carry out since they require careful and extensive mechanical debridement of the canal walls and use of copious volumes of irrigants such as aqueous sodium hypochlorite to flush out the canal. The more posterior the tooth situation within the mouth the greater the risk of failure to achieve the objectives, since the root canals morphology becomes more convoluted and adequate access becomes more difficult to achieve.

SUMMARY OF THE INVENTION

An important objective of the present invention is to simplify the treatment of dental root canals and to provide a treatment system which enables the dentist to be more confident that remnants of decay and bacterial contamination within the canal have been removed, prior to obturation of the canal to seal it.

Another object is to reduce the time normally required to prepare a root canal for obturation and also preparing the canal for alternative systems of obturating the canal which can be coordinated with the preparation of the canal.

According to one aspect of the invention there is provided a method of treating a dental root canal which comprises the steps of:

(a) gaining access to the root canal;

(b) introducing a flowable photosensitiser into the root canal;

(c) activating the photosensitiser by exposing the walls of the root canal to laser light via an optical fibre within the root canal to kill bacteria within the root canal; and (d) obturating the root canal.

As mentioned above, the root canal is first opened up and necrotic material removed by filing or reaming. One convenient method of cleaning out the root canal is by using endodontic instruments to produce a fluted, tapered tunnel. Normally, a series of instruments are used of similar length and the diameters at the tip increase sequentially. These instruments may be used both manually or, conveniently, may be fitted to a conventional rotary dental handpiece. During and after the canal shaping step, debris loosened by the mechanical debriding of the interior and walls of the canal is removed by irrigation and organic debris dissolved. Traditionally, aqueous sodium hypochlorite solution is used, e.g. at a concentration of 2~3%. These are used in copious volumes during the debriding procedure to remove solid debris or kill bacteria (Chow et al, 1983, J. Endodont. 9,475).

In the method of the present invention, sodium hypochlorite may be used for initially cleaning and flushing away loosened debris. However, an aqueous solution of the photosensitiser may alternatively be used in this step, or at least after the initial debris has been removed and the hypochlorite solution flushed away.

The next step is to introduce the photosensitiser dye into the root canal. Preferably, the photosensitiser is a toluidine blue dye which is employed in an aqueous solution, although other photosensitisers may be used as mentioned in EP 0637976. On contact with the bacteria, the dye or other photosensitiser conjugates with the bacteria and once photosensititation has occurred, the site is irradiated with light of a specific wavelength which is strongly absorbed by the photosensitiser. The wavelength of light is specific to the absorption of each photosensitiser. The activation of the dye leads to singlet oxygen release and results in death of the bacteria. It is important that the light is guided closely to areas which may be contaminated with bacteria. This is best done by introducing a light guide or optical fibre into the root canal. In order to ensure that the light is directed onto the walls of the root canal, the fibre tip should be appropriately shaped. The optic fibre may have a spherical or cylindrical surface in the region of the distal end. The production of this type of tip or emitter is described in U.S. Pat. No. 5,073,402. In essence, the tip is preferably formed by contacting the distal end of the optic fibre with a light-curable composition, which in its cured state is transparent or translucent, while passing coherent light through the fibre at a wavelength causing curing of the composition. Suitable light-curable compositions include acrylate and methacrylate monomers, including epoxy and urethane acrylates and methacrylates. Such compositions may contain photochemical initiators and free radical generating additives such as α-diketones (camphoroquinone), benzoyl peroxides and dimethyl-p-toluidine. Alternatively the tips may be constructed from light polymerisable epoxy resins as described in PCT/US98/04458, "Ternary photoinitiator system for curing Epoxy/polyol compositions" and U.S. Pat. No. 6,043,295, "Ternary photoinitiator system for curing epoxy resins". Further photopolymerisable compositions that contain epoxides include U.S. Pat. No. 4,256,868, Smith, U.S. Pat. No. 4,835,193, Hayase, U.S. Pat. No. 5,545,676, Palazzotto et al. and WO 95/14716, Neckers et al. It may also be desirable to include a minor amount of a dispersed pigment in the tip, e.g. up to about 1~2% by weight of a white pigment, such as $TiO_2$. This has a scattering effect of the light transmitted by the fibre and ensures that the walls of the canal are uniformly illuminated. A generally isotropic tip can be formed by immersing the optic fibre tip in a bath of a light-curable composition, e.g. as described in U.S. Pat. No. 5,073,402. The shape of the tip may be predetermined, e.g. a cylindrical tip may be formed by introducing the fibre tip into a mould, such as a tube, containing the polymerisable composition. By selecting a polytetrafluoroethylene (PTFE) or silicone to form the mould, it can be readily stripped away after the light-curable resin has been polymerised. A tubular mould can be used to produce a cylindrical tip. A spherical tip can be produced by the technique described in the above US patent. The optical fibre has a core, usually of glass, and a cladding which helps to enhance its strength and flexibility. Suitable claddings are plastics material such as polyamides and methacrylates. Prior to forming the tip, the end of the fibre is treated to strip cladding from the end of the fibre. A flame or concentrated acid can be used for this purpose. The stripped and cleaned end is then immersed in a bath of light-polymerisable liquid resin composition and light passed through the fibre to form a pear-shaped droplet of "soft-cured" resin. The tip is then removed from the bath and the droplet hardened by passing light down the fibre for a further period, preferably at higher intensity. Cladding is removed from the tip so that the droplet of resin adheres both to the core and to the cladding. During the hardening stage, the droplet of soft-cured resin is maintained in a no-oxygen containing atmosphere, e.g., by immersing it in an inert gas or liquid, e.g., paraffin oil.

After the root canal has been treated with the photosensitiser and irradiated with light, the root canal is dried, e.g. by aspiration and using absorbent points. The canal is then obturated using a suitable system to seal the canal. This may involve the use of conventional sealing system such as shaped gutta percha, silver or titanium points cemented with an endodontic sealer. Examples of these include zinc oxide/eugenol and calcium hydroxide based cements and also epoxy resins. Conventional obturation systems may be used such as those employing gutta percha are generally convenient. One suitable system involves introducing gutta percha in heated, softened form on a rod-like carrier into the canal. This procedure is described in European Patent Application No. 0337024. A similar procedure is described in U.S. Pat. No. 5,149,268.

Alternatively, the canal is obturated with a light-curable filling composition. The light curable composition may be cured by irradiation by light of a wavelength specific to activate the in situ system, introduced through an optical fibre positioned within the root canal. The optical fibre is generally provided with a distal tip for spreading the light substantially uniformly, and may be the same optical fibre that is used to guide light into the canal to activate the photosensitiser. However, it may be necessary to use light of a different wavelength for curing the sealant than for activating the photosensitiser. After the filling material has been cured, the optical fibre may remain entombed in the root canal as part of the obturation.

The invention also includes a kit of parts for treating a dental root canal which comprises:—

(a) a flowable photosensitiser;

(b) an optical fibre having a distal portion for emitting light and adapted for introduction into a root canal so that the tip is capable of reaching the apical region of the root canal, said optical fibre being connectable proximally with a means for generating light; and (c) obturating means for sealing the canal.

In one form of the invention, the obturating means is a flowable, light curable filling composition.

It will be appreciated therefore that in one aspect the invention makes use of a combination of a photosensitive substance and a light source operating at the appropriate wavelength to activate the photosensitiser. A further aspect of the invention is the delivery mechanism, which permits the delivery of the photosensitiser either at or near the apex of the root canal to ensure that the photosensitiser will contact the debris and bacteria. A related aspect of the invention is the provision of a specially shaped spherical or cylindrical tip to an optical fibre which permits application of light of appropriate wavelength to the region of the apex of a tooth. A still further aspect is the provision of a specially shaped optical tip to provide uniform light near the apex of the tooth. A further element is the provision of a novel sealing or filling material, which will prevent re-infection of the canal from either the access cavity or via the apical foramen. The sealing or filling material may be delivered via the novel delivery system.

As mentioned above, the pulp chamber and coronal region of the root canal is accessed in the normal way using a high speed dental drill. Alternatively, a laser may be used to expose the pulpal chamber and the entrance to the root canal. After initial estimation of canal length which may be carried out by radiography or use of electro optical detection devices, the canal opening may be increased by reaming the canal. The canal may then be irrigated with a known irrigant such as with aqueous hypochlorite or more preferably with the photosensitiser. This may be achieved using a fine tipped syringe or, alternatively, with a specialised dispensing accessory as described below. Turbulent flow may be induced when injecting the photosensitiser into the canal as described in Gooden, 1976, 2: 2571, Chow J. Endodont 1983 9.47. Effective irrigation is achieved by preparing an inwardly tapered canal to ensure the irrigants reach to the apex. This may be facilitated by the use of appropriate instruments.

After introducing the photosensitising agent into the root canal in the tooth, the agent is activated using light delivered by an optical fibre from the specific light source. The wavelength employed depends on the absorption spectra of the photosensitiser. Toluidine blue O is preferably employed as the photosensitiser and has an absorption maximum in the range of 630–660 nm. Semiconductor lasers, gallium/arsenide and helium/neon lasers may be used. The laser light may be continuous or pulsed. It has been found to be important to spread the laser light within the canal rather than focus it on a small target area. One way of achieving this is to provide an optical fibre which terminates in a tip of specific shape; this may be an isotropic tip of spherical configuration.

Another method is to provide a distal portion having curved surfaces, such as cylindrical surfaces. The light-spreading portion may be larger than the diameter of the optical fibre or substantially the same size. The light spreading portion may be formed by removing the internally reflecting outer layer of the optical fibre over a portion of the probe or by providing an extended portion of the desired shape having no internal reflecting portion. Alternatively, the internal light reflecting coating may be omitted in the desired area when forming the coating. One method of forming such a tip is described in U.S. Pat. No. 5,073,402.

Essentially, the light-spreading distal tip may be conveniently formed by moulding or casting a curable light transmissive composition on the end of the optical fibre. A spherical tip may be formed by dipping the optical fibre into a polymerisable composition and curing the adherent droplet, while supporting the droplet in a non-miscible, inert liquid. Curing may be effected by passing light of the appropriate wavelengths for curing along the optical fibre. Suitable polymerisable compositions include light curable acrylate and methacrylate compositions, including those described below as suitable sealant materials. It may be desirable to include a light-scattering material, such as a dispersed pigment in an amount of up to 5% by weight, within the polymerisable material to increase the uniformity of irradiation of the root canal. However, the cured tip will be transparent or translucent to light of the wavelength selected for sensitising the dye.

Other shaped tips may be formed by moulding or casting the desired shape onto the end of the optical fibre.

The Photosensitiser

The photosensitiser or dye is used for the disinfection of the internal surface of the root canal by placing a liquid or gel containing the photosensitiser in contact with the debris and bacteria. The interior of the root canal is then irradiated with light of an appropriate wavelength that will be absorbed by the photosensitiser.

In preferred aspects of the invention, the photosensitiser and laser combination may be applied to:—

(a) disinfection or sterilisation of the root canal after initial access has been gained to the root canal of the infected tooth; or as an adjunct to conventional preparation prior to obturate of the canal;

(b) destruction of carious microbes on the internal root surface in order to prevent reinfection.

Photosensitising agents used in this invention are generally non toxic to the target microbes in the concentrations envisaged or to the surrounding tissue. However, there is no requirement that the photosensitiser should not be toxic to the microbes. Since the exposure times are short, it may be acceptable to use compounds which have some slight toxicity to the tissue.

It is preferred that the photosensitisers used will be capable of absorption in the red end of the visible spectrum or at longer wavelength, as these wavelengths will have greater penetrating powers in the dental tissue surrounding the canal.

The preferred photosensitisers are those effective against Gram Negative bacteria associated with endodontic lesions. Common types of bacteria found in root canal infections contain facultative anaerobes and strict anaerobes and are described in Lewes MAO, McFarlane T W and McGowan D A J Medical Microbiology 21:101:1986. These include:—

Facultative Anaerobes including *Streptococcus milleri* and *Actinomyces naeslundi*. Strict Anaerobes including *Bacteroides gingivalis, Bacteroides melaninigenicus, Bacteroides oralis, Peptococcus* species and *Peptostreptoccus* species. The classification of these bacteroides type bacteria include *Porphyromonas [gingivalis* and *endodontalis]* and *Prevotella [melaninogenica* and *intermedia]*. The presence of these bacteria in an infected root canal or after inadequate cleaning will lead to infection and pain and discomfort. The function of the photosensitiser is to bind to the bacteria and to release singlet oxygen on interacting with the laser light. Of the available photosensitisers, the currently preferred is Toluidine blue O. Alternatively, aluminium disulphonated phthalocyanine chloride, methylene blue or azure blue chloride may be used. While the dye may be non specific, it can be made specific to the microbes within the root canal.

The Laser

The concentration of photoinitiator and laser power are matched to provide maximum penetration of tissue and kill rates.

The concentrations of dye range from 0.00001% to 2%. The currently preferred concentration is 0.0001 to 0.2%, especially 0.001 to 0.1%.

The preferred laser irradiation time of the photosensitiser is between 10 seconds and two minutes and the preferred exposure time is between 30 seconds and 90 seconds.

The laser power is preferably between 25 and 150 mW, the most preferred being about 80 mW. The laser power/exposure time combination may be varied to give a desired dose.

The photosensitiser solution concentration may be influenced by any extrinsic fluid and concentration may be increased to compensate for this.

In order to modify the surface of hard tissue and to enable the photosensitising agents to have maximum effect, potentiating agents may be used as adjuncts to the photosensitising solution. These may be used in conjunction with, prior to or subsequent to the photosensitising solution. These adjuncts include:—

Acids to produce a solution pH of 4.5 or above

Acids to penetrate and remove organic/inorganic debris

Wetting agents such as HEMA (hydroxyethyl methacrylate) and glutaraldehyde

Demineralising agents such as chelating agents of the type EDTA disodium.

Such materials may be citric acid, polyalkenoic and polyphosphonic acid, phosphoric acid, EDTA and HEMA or other such acids as are known for use in this technique. EDTA and citric acid have an adverse effect on the bacterial kill rate if used simultaneously with the photosensitiser. Thus, in the case of these adjuncts, they should be employed prior to or after treatment with the photosensitiser and the treated area flushed with a wash liquid prior to treatment with the photosensitiser. Phosphoric acid, particularly when buffered to a pH of 4.5 or above appears not to adversely affect bacterial kill rates when used at the same time as the photosensitisation treatment.

It is important that these agents do not interfere with the photosensitising process, in particular the use of free radical and singlet oxygen scavenging materials should be avoided.

The photosensitiser may be delivered by a syringe or by a unit dose delivery device, which may include a thin flexible tube which may be perforated along the final part of its distal end, e.g. the last 15 mm of its length. The perforated tube, whose diameter is preferably a maximum of 0.1 mm, will be inserted up the canal without binding against the walls. This will normally be within the apical third of the canal (this being the third of the root canal closest to the root apex), and as close to the apex as achievable without binding on the walls. The dye is then injected, e.g. via a unit dose cartridge, through the tube permitting the dye to coat the whole length of the walls of the root canal. The unit dose syringe and tube will then be removed and the fibre connected to a suitable light source and inserted into the canal. The photosensitiser dye will be activated by the light source.

The Filling or Sealing Material

A further aspect of the invention is that a fluid sealing agent may be syringed up through the delivery system previously described in connection with the photosensitiser. This will coat the walls of the root canal and displace air from the canal as it fills the canal through a tube or syringe tip terminating in the region of the apex. The sealing agent may then be cured using a visible light source, via an optical fibre tipped with an isotropic tip.

These may be resins such as those described as dental adhesives in Patent Application Nos. PCT/GB92/02128; PCT/GB98/00072; U.S. Pat. No. 5,172,763 and U.S. Pat. No. 5,063,257, and other curable resin systems which are employed as dental adhesive and filling materials, e.g. those described in the following patents and applications:]

EP 0356868 WO 97/00065
GB 2107341 UK 1488403
U.S. Pat. No. 5,520,725 U.S. Pat. No. 4,627,097
U.S. Pat. No. 1,428,165 U.S. Pat. No. 4,001,483

The hermetic seal after bacterial killing is an integral part of the endodontic treatment technique since it is by these means that the bacterial re-infection is minimised. This may be achieved using existing dental materials.

The preferred materials may have a viscosity which may be varied to suit the application. Preferred viscosities are from 0.33 to 1340 centipoise. Where it is used as a dentine substitute, the viscosity is similar to that of water and has mechanical properties such as flexural strength after polymerisation in the range 80 to 170 Mpa. Shrinkage during polymerisation will be in the range of 0.5 to 4.5% by volume. The sealing agent is made of a blend of resins, which will provide a range of viscosities to suit the intended application.

These may be di-methacrylates or methacrylates as set out in the patents mentioned above. The preferred resin system is a mixture of urethane dimethacrylate (UDMA), bisphenol-A-glycidyl dimethacrylate (BisGMA) and tetrahydrofurfuryl methacrylate (THFMA), which contains THFMA in the range of 30–90% by weight of THFMA. These may be in various proportions, the preferred composition being THFMA 50%, UDMA 33% and BisGMA 17%.

The material may be polymerised chemically or by application of light of a particular wavelength. Sealant materials based on light curable acrylates or methacrylates are commonly cured with light having a wavelength of about 450-470 nm.

Cold cure initiator systems which do not require the addition of external energy (heat or light) are materials such as benzoyl peroxide as an initiator and N,N-dimethyl-p-toluidine as an activator.

Preferred light activation systems are those including camphorquinone and an amine. Other activation systems may also be used.

The initiators should be present in an appropriate amount to provide an adequate level of conversion and adequate rate of conversion. They are usually present in amounts between 0.1% and 12% of the weight of the monomer mixture. Preferred values are between 0.5 and 5% by weight of the monomer mixture.

Various additives may optionally be included in the mixture such as antioxidants, stabilisers using UV inhibitors and polymerisation inhibitors, pigments and therapeutic agents such as antibiotics, corticosteroids and other medicinal agents such as metal ions.

Alternative materials such as sol-gel glasses may also be used as the sealing agents delivered in a similar manner to that described above. Other useful sealing materials include light-polymerisable epoxy resins as mentioned above and described in PCT/US98/04458 and U.S. Pat. No. 6,043,295.

The most preferred obturating materials comprise those which seal the canal by deformation under pressure. The root canal sealer which acts as a sealing agent between the canal wall and the obturating material is gutta percha. Its properties allow it to be compressed against the canal wall. The gutta percha points are matched in size to the shaped canal. The gutta percha can be laterally condensed, vertically condensed, heat or cold compacted. A range of additional techniques may be used including heat softening and adapting. Injection of warm gutta percha may also be used. The technique recommended by Tulsa Dental Co. under the name "Thermafil" might also be used to obturate the canal. Here the gutta percha is formed around a plastic pin. The gutta percha is heated and the pin and gutta percha inserted into the root canal. Pressure is applied with the plastic pin forcing the softened material into all the orifices in the canal walls.

A major advantage of the present invention is that the technique of applying laser light to the photosensitiser within the canal gives a much higher level of assurance to the dentist that residual infection has been eradicated. In part, this is because the photosensitiser is absorbed into the side passages leading from the main canal and that the laser light passes through a significant thickness of dentine.

The following is an experimental evaluation of the effectiveness of the PDT technique against organisms implicated in endodontal infections.

(i) Target Bacteria

A wide variety of bacteria have been implicated in endodontal infections. However, the current literature suggests that the most important species are the following: *Peptostreptococcus micros, Fusobacterium nucleatum, Prevotella intermedia, Streptococcus intermedium* and *Streptococcus mutans*.

(ii) Experimental Procedures

The aim of this part of the work was to determine whether PDT is able to achieve substantial kills of the target organisms. The criteria for success would be the killing of all target organisms by low light doses in the presence of clinically-acceptable concentrations of toluidine blue O (TBO).

Two key experimental parameters were selected—TBO concentration and light energy dose. In order to investigate the effects of these parameters on bacterial killing, a quantitative assay established and employed in previous studies was used.

The basic experimental protocol consisted of the following. The target organisms were grown for 24-48 h (depending on the particular species) in fastidious anaerobe broth at 37° C. in an anaerobic cabinet. 30 µl aliqquots of a suspension of each organism in 0.85% (w/v) saline were then transferred to wells of a 96-well, round-bottomed micro-titre plate and an equal volume of a saline (0.85% w/v) solution of the TBO added to each well. Duplicate wells were exposed to light from the laser diode (following immersion of the tip of the optical fibre in the suspension) for the requisite period of time. Control wells containing the microbial suspension plus 0.85% (w/v) saline in place of the TBO were treated in an identical manner to determine the effect of laser light along at a wave length of 640 nm on bacterial viability. A further four wells, identical to those described above, were prepared and kept in the dark. Hence the effect on bacterial viability of the TBO alone was ascertained. After irradiation of appropriate wells, serial dilutions of the contents of each well were prepared in sterile nutrient broth and 50 µl aliquots spread over the surfaces of blood agar plates. After anaerobic incubation of the plates for up to 7 days at 37° C. the resulting colonies were counted.

Using the method described above the following results were obtained on anaerobic organisms.

TABLE 1

Exposure Time 30 sec Laser Power 80 mW

| Dye Concentration [µg/mL] | Organism | Initial cfu | % Bacterial kill | Mean |
|---|---|---|---|---|
| 20 | Streptococcus intermedius | 1.46E8 4.90E10 | 99.914 99.286 | 99.6 |
| 20 | Peptostreptococcus micros | 3.23E8 1.94E9 | 99.901 98.865 | 99.38 |
| 20 | Fusobacterium nucleatum | 6.98E6 | 99.959 | |

TABLE 2

Exposure Time 60 sec Laser Power 80 mW

| Dye Concentration [µg/mL] | Organism | Initial cfu | % Bacterial kill | Mean |
|---|---|---|---|---|
| 10 | Streptococcus intermedius | 2.85E8 3.56E8 | 99.9997 99.9958 | 99.998 |
| 20 | Peptostreptococcus micros | 2.45E9 2.49E8 | 99.999 99.996 | 99.998 |
| 20 | Fusobacterium nucleatum | 1.32E7 1.57E7 | 99.934 99.841 | 99.998 |

Lethal Photosensitisation of *Streptococcus mutans* in a Saline Suspension.

Experiments have been carried out using a range of concentrations of Toluidene blue O (TBO). These concentrations have been inoculated into a saline suspension of *Streptococcus mutans* and then irradiated using the laser equipment shown in the accompanying drawings. A range of power densities and exposure times were evaluated. Full details of exposure times and laser power densities and dye concentrations assessed are set out in Table 3. Wavelength was 640 nm.

TABLE 3

| Dye Concentration [µg/ml] | Dye/Bacteria Suspension Volume [µ/L] | Laser Power [mW] | Exposure Time [sec] |
|---|---|---|---|
| 50 | 200 | 80 | 30 |
| 50 | 200 | 48 | 30 |
| 50 | 200 | 15 | 30 |
| 50 | 200 | 80 | 60 |
| 50 | 200 | 48 | 60 |
| 50 | 200 | 15 | 60 |
| 50 | 200 | 15 | 90 |
| 20 | 200 | 80 | 30 |
| 20 | 200 | 15 | 30 |
| 20 | 200 | 80 | 60 |
| 20 | 200 | 15 | 90 |
| 20 | 200 | 15 | 60 |
| 20 | 50 | 40 | 10 |
| 20 | 50 | 40 | 20 |
| 20 | 50 | 40 | 30 |
| 5 | 50 | 40 | 20 |
| 5 | 50 | 40 | 50 |
| 5 | 50 | 40 | 80 |

Dye solutions were made up freshly on each occasion using distilled water. Initially, 100 µl of a saline suspension of *Streptococcus mutans* was added to a micro well of a microtitre plate. These were derived from *Streptococcus mutans* NCTC 10449 and suspension was made up to give a concentration of bacteria ranging between $10^8$ to $10^9$ colony forming units (cfu). [These had an optical density of approximately 0.10]. This solution was then gently agitated for the remainder of the experiment. To this was added either 100 µl of TBO or saline. Saline acted as a control. 30 seconds after the addition of the dye, the isotropic probe was immersed in suspension and irradiation carried out at the range of exposure time/power density combinations indicated in Table 3.

Aluminium foil was wrapped around the base of each well on the microtitre plate to prevent laser irradiation affecting wells adjacent to that being treated.

After irradiation, the number of survivors in each well was determined by viable counting on tryptone soya agar. 100 µl of liquid from the micro well was removed and diluted progressively tenfold. The diluted suspension was then cultured on the tryptone soya agar plate for 24 hours. Plates were then selected with densities of colony forming units of between 50-300 cfu and these were examined for surviving bacteria over the whole of the sample on the plate.

Results

A range of kill levels was achieved with the different combinations of laser power exposure time and dye concentration. This shows that the kill levels required may be achieved at certain laser power/exposure time/dye concentrations. There is a range of combinations, which may be appropriate for use clinically.

Phase 1:

An exposure time of thirty seconds was arbitrarily established as the baseline value to be examined. The laser parameters were defined by the outputs of the machine and 80 and 15 mw selected as the outer limits for initial evaluation. Dye concentrations were fixed at values that had previously been established for penetration of dentine.

The results of the four stages are set out below.

Exposure Time 30 Seconds
Stage 1: Maximum dye concentration and Maximum laser power

| Dye Concentration [μg/mL] | Laser Power [mW] | Initial CFU | % Bacterial kill | Mean |
|---|---|---|---|---|
| 50 | 80 | E9-E10 | 93.11 | 89.71 |
|  |  |  | 86.32 |  |

This indicated that there were very substantial kills but total kills were not on the 99.9% value at this particular exposure time.

Stage 2: Minimum dye concentration and Minimum laser power

| Dye Concentration [μg/mL] | Laser Power [mW] | Initial CFU | % Bacterial kill | Mean |
|---|---|---|---|---|
| 20 | 15 | 1.1E9 | 0 | 20.0 |
|  |  |  | 40.0 |  |

This showed that the minimum output from laser and low dye concentration did not produce adequate kills.

Stage 3: Minimum dye concentration and Maximum laser power

| Dye Concentration [μg/mL] | Laser Power [mW] | Initial CFU | % Bacterial kill | Mean |
|---|---|---|---|---|
| 20 | 80 | E9-E10 | 99.99 | 99.99 |
|  |  |  | 99.99 |  |

This demonstrated that the kill levels, which were required, were achievable at this laser power and dye concentration Stage 4: Maximum dye concentration and Minimum laser power

| Dye Concentration [μg/mL] | Laser Power [mW] | Initial CFU | % Bacterial kill | Mean |
|---|---|---|---|---|
| 50 | 15 | 2.1E10 | 0 | 7.05 |
|  |  | 2.8E9 | 14.1 |  |

This shows that maximum dye concentration and minimum laser power produced inadequate kills.

CONCLUSIONS

From this is became apparent that successful kills were obtainable with the minimum dye concentration and maximum laser output. Increasing the dye concentration at that laser power reduced the kill rate. From this it was deduced that the maximum dye concentration was in excess of that required and that better results were achievable at lower concentrations. This was confirmed by the stages two and four where although the kill rates were not very high, the higher dye concentrations produced lower kill rates.

Further work was then carried out using different exposure time and laser energy densities in an attempt to establish the range of combinations, which would prove to be effective. For clarity, the results have been reported in sequence for increasing exposure time.

Exposure time: 10 sec

| Dye Concentration [μg/mL] | Laser Power [mW] | Initial CFU | % Bacterial kill | Mean |
|---|---|---|---|---|
| 20 | 40 | 2.6E7 | 20.23 | 36.34 |
|  |  |  | 52.45 |  |

This was regarded as unsuitable for use. It was not repeated with a lower dye concentration as the increase in kill rates expected was considered to be insufficient to achieve and the exposure time was increased.

Exposure time: 20 sec

| Dye Concentration [μg/mL] | Laser Power [mW] | Initial CFU | % Bacterial kill | Mean |
|---|---|---|---|---|
| 5 | 40 | 1.7E7 | 0 | 30.1 |
|  |  | 1.1E8 | 60.3 |  |
| 20 | 40 | 3.0E7 | 79.36 | 81.1 |
|  |  | 1.8E7 | 82.90 |  |

The exposure time of 20 seconds produced kill rates which were substantially higher. At the 20 μg/mL dye concentration tested here 80% kill levels were obtained.

Exposure time: 50 sec

| Dye Concentration [μg/mL] | Laser Power [mW] | Initial CFU | % Bacterial kill | Mean |
|---|---|---|---|---|
| 5 | 40 | 7.1E7 | 84.43 | 87.14 |
|  |  | 1.3E8 | 89.85 |  |

The exposure time was extended to 50 seconds with a low dye concentration and low laser power. The kill rates while not being total were extensive. This indicated that the lower dye concentration [5 μg/ml] is probably the bottom level that is applicable. It would require a high laser output and longer exposure time for total killing to be achieved.

Exposure time: 60 sec

| Dye Concentration [μg/mL] | Laser Power [mW] | Initial CFU | % Bacterial kill | Mean |
|---|---|---|---|---|
| 20 | 15 | 1.2E9 | 86.32 | 52.29 |
|  |  | 1.1E9 | 18.26 |  |
| 20 | 80 | E9-E10 | 99.99 | 99.99 |
|  |  |  | 99.99 |  |
| 50 | 15 | 1.3E9 | 12.0 | 12.16 |
|  |  | 2.8E9 | 12.32 |  |
| 50 | 48 | 2.3E10 | 99.76 | 99.78 |
|  |  | 1.3E9 | 99.8 |  |
| 50 | 80 | E9-E10 | 99.99 | 99.99 |
|  |  |  | 99.99 |  |

When the exposure time was extended to 60 seconds with a range of laser powers and dye concentrations, it became apparent that kill rates were high for a range of dye concentrations and laser power outputs. It was apparent that the minimum laser power that was successful in achieving kill rates in the region of $10^9$ was 45 mW at this time interval.

The accompanying drawings illustrate the manner in which the invention may be carried into effect.

The tooth (1) is first drilled to access the entrance (2) to the infected root canal (3), and the canal opened up and debrided using conventional instruments. Loose debris is suctioned away and, optionally, the canal is flushed with a hypochlorite solution and then with water. A photosensitiser solution, e.g. Toluidine blue O, in dilute aqueous solution (concentration about 20 μg/ml) is then introduced into the root canal using a fine-tipped syringe having an obliquely angled tip, or a disposable dispenser such as shown in FIG. 2a or 3. Referring to FIG. 3, the dispenser comprises a thin-walled cannula (10) having a reservoir (11) for photosensitiser solution attached to its proximal end. The connection between the reservoir and the cannula is sealed with a frangible membrane 12. At its distal end, the cannula is perforated with small holes (13) which permit the escape of liquid from the cannula. In use, the cannula is inserted into the root canal until the distal end is close to the apex of the canal. Photosensitiser is discharged into the root canal by pressing on the reservoir (11), thus causing the membrane to rupture and liquid to flow out of the distal end and through the perforations (13). The perforations (13) ensure that the walls of the root canal are wetted with photosensitiser solution. Preferably, the photosensitiser is allowed to remain in contact with the root canal to permit the photosensitiser to be absorbed by bacteria within the canal, normally about 20 to 40 seconds. The dispenser is then removed and an optical fibre (20), as shown in FIG. 2, is introduced into the root canal (3) and laser light having a wavelength of about 630/640 nm guided into the canal.

Figure 2:
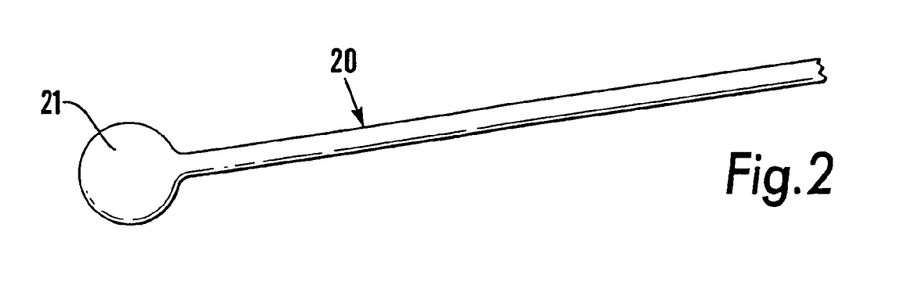
FIG. 2 is a enlarged sectional view of the optical fibre.
Figure 3:
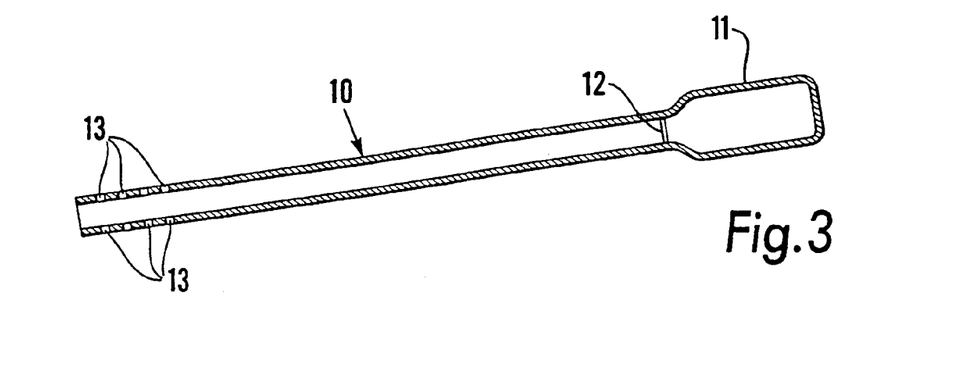
FIG. 3 is a section through a single dose device for delivering a photosensitiser solution into the root canal.

As can be seen best in FIG. 2, the optical fibre is formed with a transparent distal spherical portion (21), typically of about 800 microns diameter. This has the effect of diffusing light passed down the fibre and ensures that light emerging at the tip (21) is scattered uniformly around and in upward and downward directions in the root canal.

It may be desirable to move the tip of the optical fibre relatively to the canal, either stepwise or continuously, while irradiating the interior of the canal. For example, the tip may be inserted initially to the apex of the canal and then gradually withdrawn, while irradiating the canal. This may be facilitated by the fibre carrying incremental markings on its external surface similar to the tip dimensions. The operator may withdraw the tip incrementally, using the marks to ensure that irradiation of the photosensitiser is carried out over the whole canal length. Instead of an optical fibre having a spherical tip, a fibre having a generally cylindrical distal part may be used. For example, the tip may comprise a 3 mm long cylindrical tip having a diameter of about 200 to 500 microns, preferably 200 to 300 microns. This has approximately the same area as the spherical tip referred to above.

The optical fibre itself typically has a diameter of about 200 to 800 microns, preferably 200 to 500 microns. The fibre may be protected by an outer tube of plastic or metal, with the tip projecting from the outer protective tube. The outer tube may be tapered in the same sense as the prepared root canal.

Figure 1:
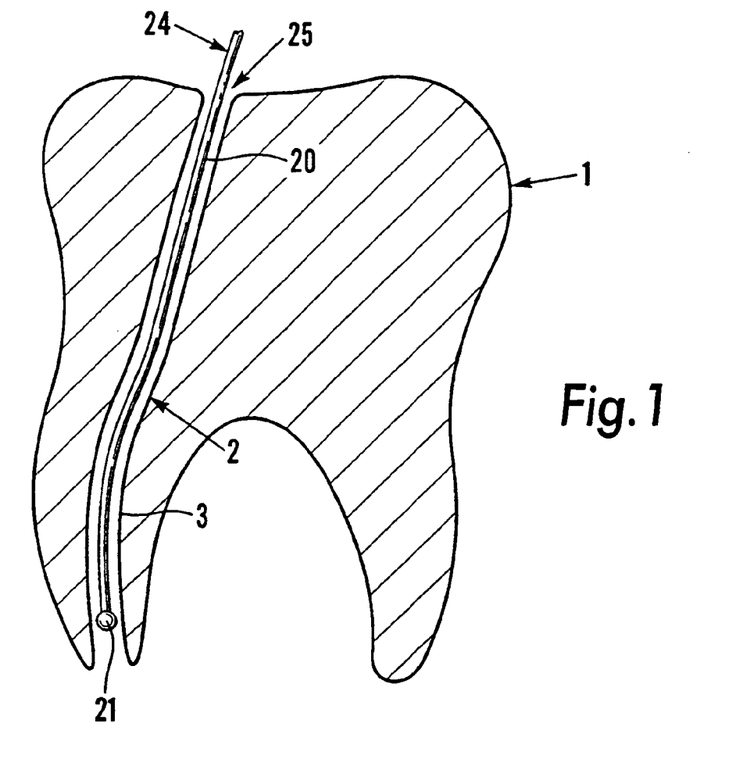
FIG. 1 is a schematic longitudinal cross-section through a tooth with one form of optical fibre and tip in place in a root canal.
Figure 2A:
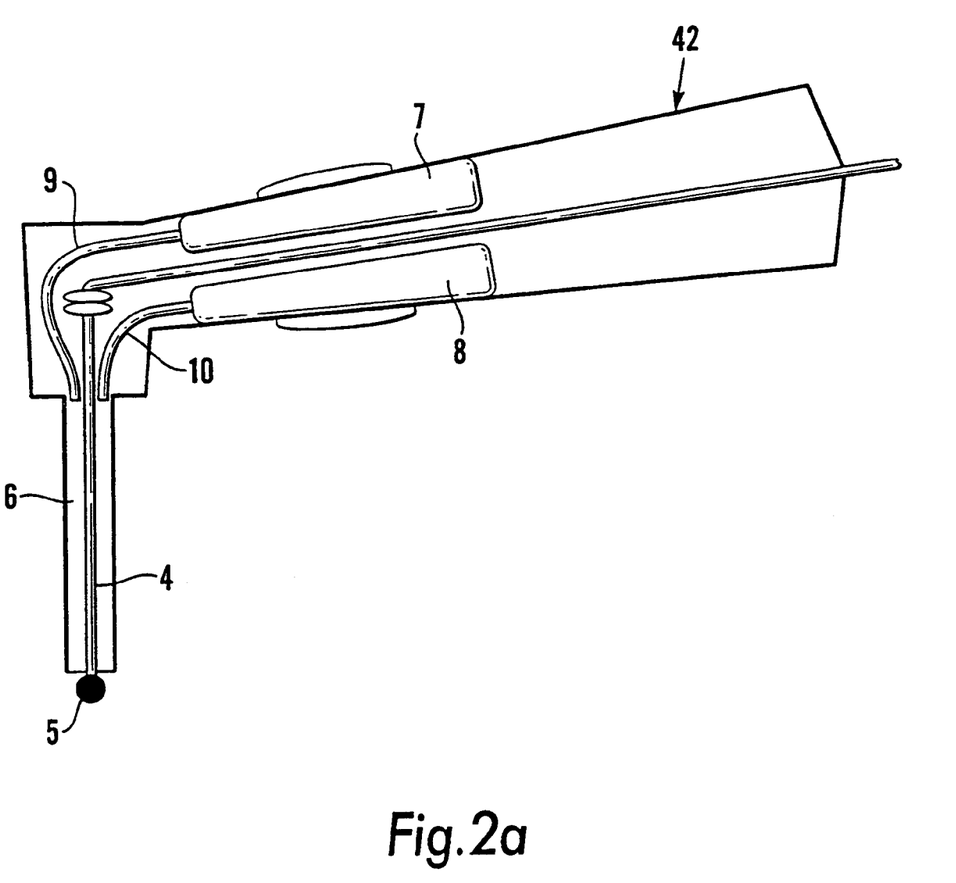
FIG. 2a is a schematic view of a dental handpiece fitted with an optical fibre and tip and a tube for introducing photosensitiser into a root canal.

FIG. 2(a) shows a developed form of the system shown in FIGS. 1, 2 and 3. The handpiece (42) has a "plug in" optic fibre (4) having an isotropic tip (5). The fibre is received as a snap-fit in the handpiece (42) and is optically connected through the handpiece to a laser source in the console (41). Surrounding the optic fibre is a hollow tube (6). Contained within the handpiece are reservoirs (7) and (8) filled, respectively, with photosensitiser dye and sealant composition. Feed tubes (9) and (10) connect the reservoirs to the tube (6). The reservoirs may be squeezable pouches so that on applying pressure to the respective pouch, dye or fluid resin can be injected as required into the tube (6) and thence into the prepared canal (2) in the tooth. Preferably, the reservoirs, fibre tip and tube are disposable.

Figure 4:
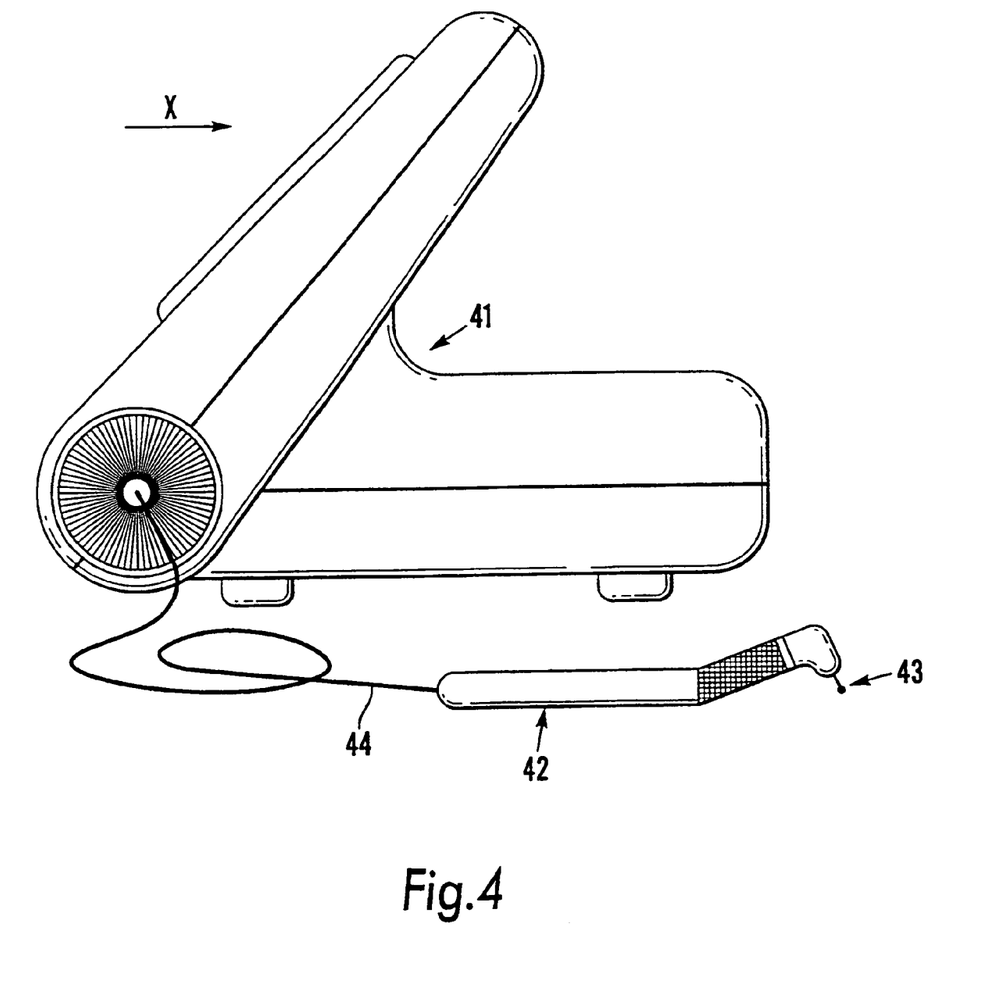
FIG. 4 is a perspective view of a laser housing connected to a dental handpiece.
Figure 5:
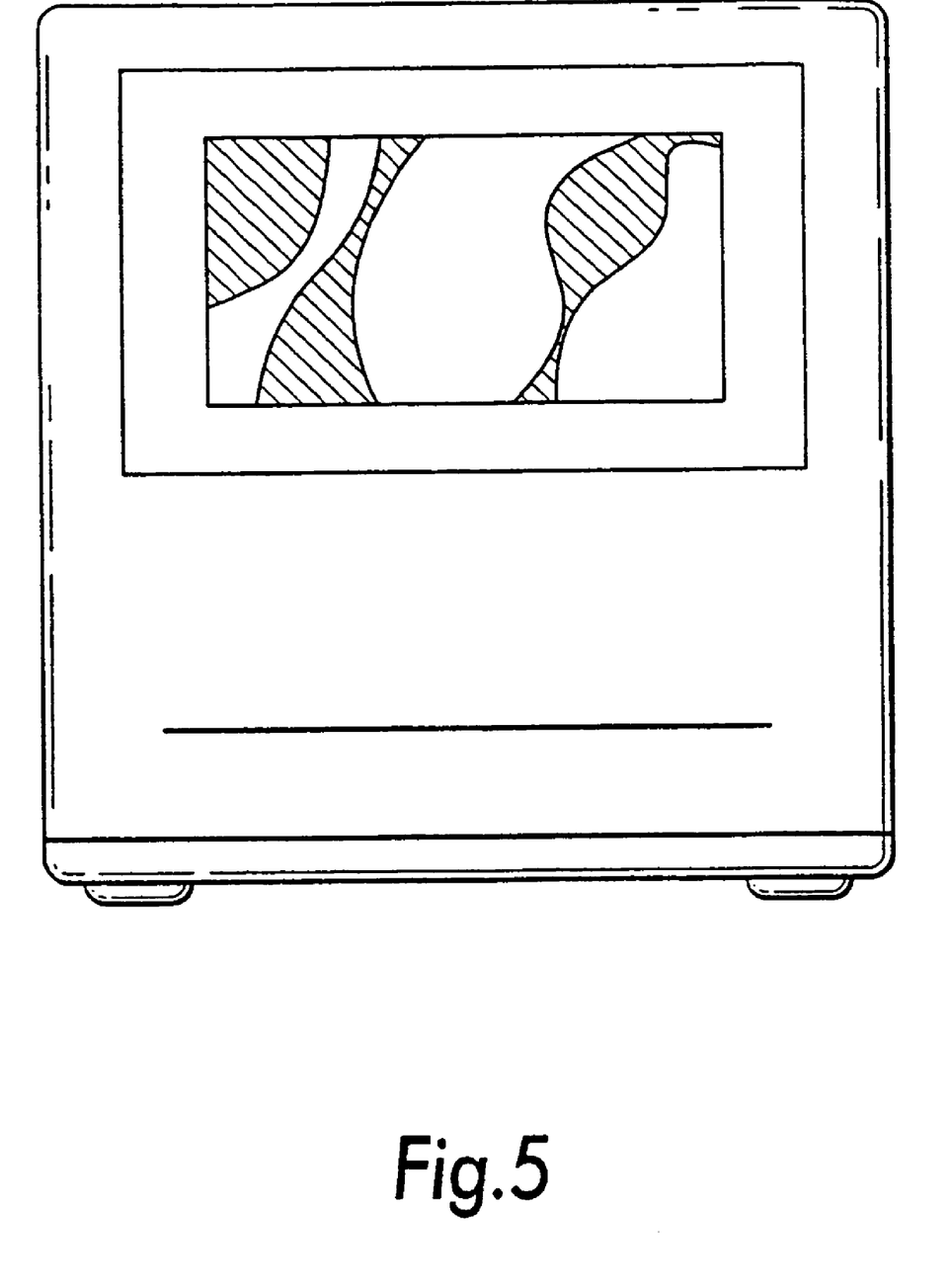
FIG. 5 is a view in the direction of the arrow "X" in FIG. 4.
Figure 6:
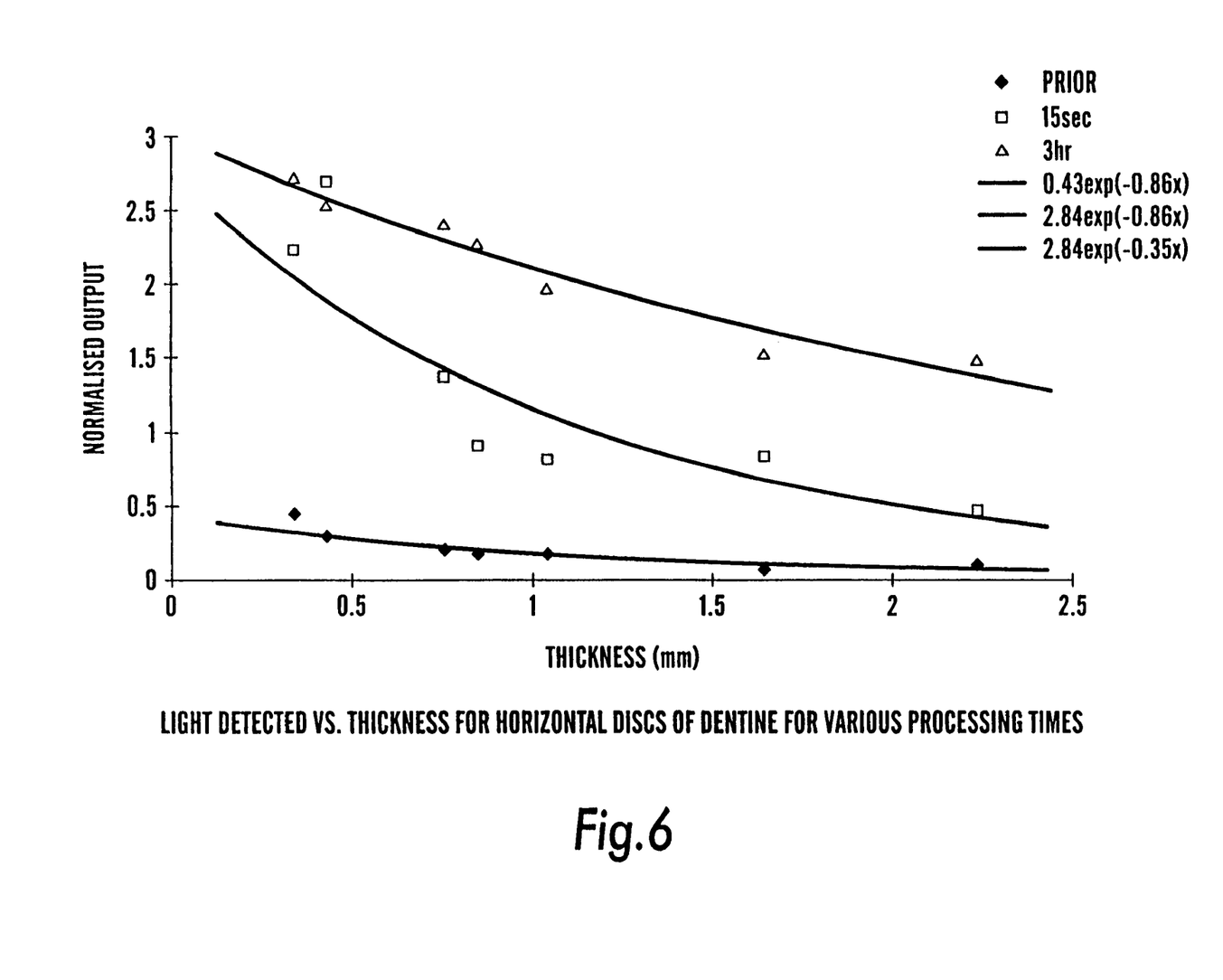
FIG. 6 is a graph showing the effect of increasing the light transmission of carious dentine by demineralisation with EDTA.

A more developed version of the laser console and a dental handpiece carrying the optical fibre is shown in FIGS. 4 and 5. FIG. 4 shows a perspective view of the laser housing (41) linked to a dental handpiece (42). An optical fibre (43) is held in the part of the handpiece which will be introduced into the patient's mouth. The optical fibre (43) is a disposable "plug in" element which carries an isotropic tip as described above. Housing (41) contains laser generating equipment whose output is connected to a flexible heavy duty optical fibre within the handpiece, the output from the fibre (44) is connected to the disposable fibre (43). Two laser sources may be accommodated in the housing (41), one capable of emitting laser light at a wavelength of about 670 nm for effecting the photosensitising treatment, and the other capable of emitting laser light for curing the resin sealant. Light guides and a beam splitter may be provided so that light from each laser source can be selectively switched to the tip (43). The fibre tip may be changed after the photosensitising treatment has been carried out and fresh tip plugged into the handpiece in order to carry out curing of the resin sealant.

FIG. 5 shows a control panel (45) having a touch screen (46) for programming the laser power and duration of treatment. For convenience, the apparatus can be made in portable form and incorporate a rechargeable battery.

After the photosensitiser has been irradiated with laser light for a sufficient period to ensure sterilisation of the interior of the canal (usually 30 seconds to 1 minute at a laser power of between 40-80 mW), the optical fibre is removed.

It may be desirable at this point to aspirate photosensitiser from the canal.

A fluid sealing or filling composition is then introduced into the canal. For this purpose, a unit dose dispenser such as that shown in FIG. 2a may be used. An optical fibre such as shown in FIG. 2a may then be introduced into the root canal and light passed down the fibre to cure the sealant material. This will hermetically seal the root canal from reinfection. The sealant material may incorporate a radio-opaque filler material, such as a barium or strontium salt, e.g. the fluoride. It may further contain amine fluoride. The projecting part of the optical fibre may then be cut off and the access hole may be filled with a conventional dental filling material such as an amalgam or glass ionomer resin.

Experiments with slices of dentine cut from extracted human teeth have shown that it is desirable to pretreat a canal with a demineralisation solution, e.g. of EDTA prior to the photosensitisation treatment. Even a short pre-treatment with EDTA, e.g. as a 0.1 molar aqueous solution, substantially increases the distance through which the laser light can pass. Even pre-treatment of the dentine with 0.1 molar EDTA or other demineralisation solution for as little as 15 seconds increased the depth of light transmission and dye penetration significantly. This is an important finding and enables the dentist to be confident that bacteria has been killed in passages leading from the canal in the treated tooth. The effect of demineralisation treatment on the light transmission and dye adsorption is shown graphically in FIG. 5. The effect of the demineralisation additive appears to be self-limiting in that the maximum demineralised area extends essentially only to the boundary of the dentine affected by a carious lesion.

Alternatively, the sterilised canal may be sealed by means of gutta percha plugs supported on a plastic or metal rod-like carrier as described in EPA 0337024 or U.S. Pat. No.5,149,268.

What is claimed is:

1. A dental root canal disinfection system, the system comprising:
   a flowable photosensitizer;
   a laser source that generates light at a wavelength which is capable of being absorbed by the flowable photosensitizer;
   an optical fiber coupled to the laser light, wherein the optical fiber is adapted for introduction into the dental root canal, and wherein the optical fiber has a portion at a distal end opposed to the laser source that is shaped to uniformly and simultaneously spread laser light both perpendicularly around and along the dental root canal.

2. The system of claim 1, wherein the optical fiber includes a tip capable of reaching an apical third region of the dental root canal.

3. The system of claim 1, wherein the portion at the distal end of the optical fiber comprises a cylindrical portion.

4. The system of claim 1, wherein the portion at the distal end of the optical fiber comprises a spherical portion.

5. The system of claim 1, wherein the optical fiber has a substantially isotropic tip.

6. The system of claim 1, wherein the distal portion of the optical fiber comprises a translucent polymer composition containing a dispersed pigment in an amount sufficient to cause said laser light transmitted by the optical fiber to be scattered around the dental root canal.

7. The system of claim 6, wherein the distal portion of the optical fiber comprises a light-curable polymerizable composition on an end of the optical fiber.

8. The system of claim 1, wherein the flowable sensitizer comprises an aqueous solution of a dye.

9. The system of claim 1, wherein the flowable sensitizer comprises an aqueous solution of Toluidine Blue.

10. The system of claim 9, wherein a concentration of the Toluidine Blue is in a range between 0.00001% to 2%.

11. The system of claim 9, wherein a concentration of Toluidine Blue is in a range between 0.0001% to 2%.

12. The system of claim 9, wherein a concentration of Toluidine Blue is in a range between 0.001% to 0.1%.

13. The system of claim 1, further comprising means for obturating the dental root canal.

14. The system of claim 13, wherein the means for obturating comprises at least one sealant selected from the group consisting of a preformed plug of gutta percha, silver points, and titanium points.

15. The system of claim 13, wherein the means for obturating comprises gutta percha supported on a rod-like support.

16. The system of claim 13, wherein the means for obturating comprises a light-curable resin composition placed in the dental root canal.

17. The system of claim 16, wherein the laser light transmitted through the optical fiber is effective to irradiate and cure the light-curable resin composition located within the dental root canal.

18. A method of treating a dental root canal, the method comprising:
   gaining access to the dental root canal;
   introducing a flowable photosensitizer into the dental root canal; and
   uniformly and simultaneously exposing both walls of the dental root canal and an apex region of the dental root canal to light at a wavelength that is capable of being absorbed by the flowable photosensitizer,
   wherein said exposing the walls activates the flowable photosensitizer and disinfects the dental root canal by killing bacteria within the dental root canal,
   wherein said exposing the walls of the dental root canal comprises using an optical fiber arranged within the dental root canal.

19. The method of claim 18 wherein the flowable sensitizer comprises an aqueous solution of a dye.

20. The method of claim 18, wherein the flowable sensitizer comprises an aqueous solution of Toluidine Blue.

21. The method of claim 20, wherein said introducing a flowable photosensitizer into the dental root canal comprises introducing said Toluidine Blue in an amount in the range of 0.00001% to 2%.

22. The method of claim 20, wherein said introducing a flowable photosensitizer into the dental root canal comprises introducing said Toluidine Blue in an amount in the range of 0.0001% to 2%.

23. The method of claim 20, wherein said introducing a flowable photosensitizer into the dental root canal comprises introducing said Toluidine Blue in an amount in the range of 0.001% to 0.1%.

24. The method of claim 18, wherein said using an optical fiber comprises spreading light around and along the dental root canal through a cylindrical portion at an end of the optical fiber.

25. The method of claim 18, wherein said using an optical fiber comprises spreading light around and along the dental root canal through a spherical portion at an end of the optical fiber.

26. The method of claim 18, wherein said using an optical fiber comprises using an optical fiber having a substantially isotropic tip.

27. The method of claim 18, wherein said optical fiber comprises a distal portion comprising a translucent polymer composition having a dispersed pigment in an amount sufficient to cause a laser light transmitted by the optical fiber to be scattered around the dental root canal.

28. The method of claim 18, wherein said optical fiber comprises a portion including a light-curable polymerizable composition on an end of the optical fiber.

29. The method of claim 18, further comprising obturating the dental root canal.

30. The method of claim 29, wherein said obturating the dental root canal comprises placing a seal in the dental root canal selected from the group consisting of at least one of a plug of gutta percha, silver points, and titanium points.

31. The method of claim 29, wherein said obturating the dental root canal comprises placing gutta percha supported on a rod-like support in the dental root canal.

32. The method of claim 29, wherein said obturating comprises using a light-curable resin composition to fill the dental root canal.

33. The method of claim 32, further comprising irradiating and curing the light-curable resin composition using light coupled through an optical fiber within the dental root canal.

34. The method of claim 32, further comprising activating the flowable photosensitizer and curing the light-curable resin composition using laser light coupled through an optical fiber within the dental root canal.

35. The method of claim 18, wherein said exposing comprises exposing the walls of the dental root canal to a laser light.

* * * * *